(12) United States Patent
Zhang et al.

(10) Patent No.: US 7,939,334 B2
(45) Date of Patent: May 10, 2011

(54) SIMULTANEOUS ANALYSIS OF CHLORIDES AND SULFIDES BY LOW PRESSURE ION EXCLUSION CHROMATOGRAPHY

(75) Inventors: Xinshen Zhang, Chengdu (CN); Lingyun Yu, Chengdu (CN); Xiaoping Jiang, Chengdu (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 12/695,852

(22) Filed: Jan. 28, 2010

(65) Prior Publication Data
US 2010/0267159 A1  Oct. 21, 2010

(30) Foreign Application Priority Data
Apr. 15, 2009  (CN) .......................... 2009 1 0058936

(51) Int. Cl.
*G01N 33/18* (2006.01)
*G01N 33/00* (2006.01)
*G01N 30/02* (2006.01)

(52) U.S. Cl. ........ 436/121; 436/119; 436/120; 436/124; 436/125; 436/161; 436/164; 436/172

(58) Field of Classification Search .......... 436/119–121, 436/124–125, 161, 164, 172
See application file for complete search history.

(56) References Cited

U.S. PATENT DOCUMENTS

| 5,140,527 A * | 8/1992 | Jones et al. ...................... 702/27 |
| 2006/0039827 A1 * | 2/2006 | Zhang et al. .................... 422/70 |
| 2007/0034572 A1 * | 2/2007 | Oh et al. ........................ 210/656 |

OTHER PUBLICATIONS

Martensson, L. et al, Agriculture, Ecosystems and Environment 1999, 75, 101-108.*
Channer, D. M. DeR et al, Chemical Geology 1999, 154, 59-82.*
Zhou, B. et al, Journal of Chromatography B 2007, 852, 278-281.*

* cited by examiner

*Primary Examiner* — Arlen Soderquist
(74) *Attorney, Agent, or Firm* — Beyer Law Group LLP

(57) ABSTRACT

A process for simultaneous assay of chlorides and sulfides by low pressure ion exclusion chromatography is provided, and in said process an analytic apparatus comprising a sampling valve, a sampling loop, an ion exclusion column and an analytic detection flow path is used, and said process comprises the following steps: (1) in the analytic detection flow path, the mixture of developer $R_1$ and developer $R_2$ mixes with Eluent C and then enters into a reactor, and the mixing is continued under heating. The resulting mixture flows into the optical flow cell and a baseline is mapped accordingly; (2) a testing sample S flows into the sampling loop through a sample flow path and the sampling valve, and under the drive of Eluent C, flows into the ion exclusion column from the sampling loop, and enters into the analytic detection flow path through the ion exclusion column; developer $R_1$ and developer $R_2$ each enter into the analytic detection flow path through respective developer flow path and mix with each other in the analytic detection flow path. The mixture of developer $R_1$ and developer $R_2$ mixes with the Eluent C carrying the testing sample and then enters into the reactor, and the mixing is continued under heating and a reaction takes place. The reacted mixture flows into the optical flow cell and a spectrogram of the testing sample is mapped accordingly.

8 Claims, 3 Drawing Sheets

Analyzing Status

Sampling Status

Analyzing Status

SIMULTANEOUS ANALYSIS OF CHLORIDES AND SULFIDES BY LOW PRESSURE ION EXCLUSION CHROMATOGRAPHY

FIELD OF THE INVENTION

This invention relates to an analytic process for chlorides and sulfides in aqueous solutions, especially a simultaneous analytic process for chlorides and sulfides.

BACKGROUND OF THE INVENTION

As a pollutant to the environment, chloride ions will form carcinogen chloroform when combining with the organisms in water, and chloride ions with a high concentration in water will impair the crops. Also, chloride ions having a high activity will render black metals and non-ferrous metals to be dot-erosive. Further, the sulfur-containing substances in the nature, upon the action of microorganisms, will decompose into sulfide. A large amount of sulfides are also contained in industrial wastewater from such as tannery, crude oil, paper making and chemical plants. The sulfides can cause the sensory organs to be deteriorated due to the dissipation of hydrogen sulfide in air, cause oxygen in water to be consumed and aquatic life dead.

According to Chinese National Standard (GB 11896-89), the assay of chlorides in water is carried out by silver nitrate titration method. Specifically, it is carried out as follows: in the pH range of from neutral to weak alkaline (pH 6.5-10.5), the chloride is titrated by silver nitrate with potassium chromate being the indicator. After the chloride ions are firstly completely precipitated, the chromate is then precipitated in the form of silver chromate, showing a color of brick red, which signifies the end of the titration. However, there are several problems in the method: (1) time-consuming and complicated procedures due to the manual operations in each of the steps, (2) a large consumption of chemicals, silver nitrate is harmful to the operators due to its toxicity, (3) the resistance to the interference of other ions in the assay is inferior. Additionally, there are other methods such as flow injection method (Mercuric Thiocyanate Method and Silver Ion Turbidimetric Method) and Ion Chromatography using anionic column for separation or electrical conductivity detector for detection (see Determination of Chloride Ion in Air Pollution Control Residues by Ion Chromatography, Zhangheng, etc., MODERN SCIENTIFIC INSTRUMENT, 2008(4), pages 118-119).

According to Chinese National Standard (GB 16489-1996), the assay of sulfides in water is carried out by methylene blue spectrophotometric method. Specifically, it is carried out as follows: the sample containing sulfides is firstly acidified, and the sulfide is converted into hydrogen sulfide, which is purged by nitrogen and transferred into a developer tube containing zinc acetate-sodium acetate solution, where the reaction with N,N-dimethyl-p-phenylenediamine and ammonium iron sulfate proceeds to form a blue complex methylene blue. The absorbency is determined at a wavelength of 665 nm, and the result is expressed as the apparent concentration of sulfide. However, there are several problems in the method: (1) time-consuming and complicated procedures due to the manual operations in each step, (2) a large consumption of chemicals, (3) relatively a large error for the determination and a low repeatability. In addition, on-line automatically detection methods are reported home and abroad, such as Lead Acetate Paper Strip Method, Chromatography Flame Photometric Detector Method (FPD), Ultraviolet Fluorescent Measurement and Gas Chromatography-Sulfur Chemiluminescence Detector (GC-SCD) etc.

The above mentioned manual methods and automatically analytic methods are only used to detect chlorides or sulfides, while they cannot be used to obtain the results of chlorides and sulfides in an aqueous sample simultaneously.

SUMMARY OF THE INVENTION

An object of the invention is to provide a method for automatic assay of chlorides and sulfides in environmental aqueous sample simultaneously to overcome the disadvantages of the method in the prior art. The method of the invention not only meets the requirements for both sensitivity and accuracy of the simultaneous assay of chlorides and sulfides in environmental aqueous sample, but also is easier to carry out, faster in analyzing and less consumption for chemicals.

The low pressure ion exclusion chromatography for simultaneous assay of chlorides and sulfides in the invention is operated under low pressure, an ion exclusion column (cationic column) is provided in an analytic apparatus, and a simultaneous analysis can be achieved since the chloride ions and sulfide ions in an aqueous sample respectively enter into an analytic detection flow path due to the different migration rate in the ion exclusion column based on the ion exclusion principle (the peak of chlorides is the former and the peak of sulfides is the latter).

The low pressure ion exclusion chromatography for simultaneous assay of chlorides and sulfides in the invention adopts an analytic apparatus comprising a sample flow path, an eluent flow path, a developer flow path, a sampling valve, a sampling loop, an ion exclusion column and an analytic detection flow path. The working pressure of the analytic apparatus is $2 \times 10^5$-$3 \times 10^5$ Pa, and said analytic detection flow path includes a mixer, a reactor and an optical flow cell. Said process comprises the following steps:

(1) Eluent C flows through the eluent flow path, the sampling valve, the ion exclusion column and enters into the analytic detection flow path; developer $R_1$ and developer $R_2$ respectively enter into the analytic detection flow path through each developer flow path and mix with each other in the analytic detection flow path. In the analytic detection flow path, the mixture of developer $R_1$ and developer $R_2$ mixes with Eluent C and then enters into the reactor, and the mixing is continued under heating. The resulting mixture flows into the optical flow cell and a baseline is mapped accordingly;

(2) a testing sample S flows into the sampling loop through the sample flow path and the sampling valve, and under the drive of Eluent C, flows into the ion exclusion column from the sampling loop, and enters into the analytic detection flow path through the ion exclusion column; developer $R_1$ and developer $R_2$ respectively enter into the analytic detection flow path through each developer flow path and mix with each other in the analytic detection flow path. In the analytic detection flow path, the mixture of developer $R_1$ and developer $R_2$ mixes with the Eluent C carrying the testing sample and then enters into the reactor, and the mixing is continued under heating and a reaction takes place. The reacted mixture flows into the optical flow cell and a spectrogram of the testing sample is mapped accordingly;

(3) a series of standard samples with known concentrations of chlorides and sulfides are used to replace the testing sample, and steps (1) and (2) are repeated so as to obtain a series of spectrograms of the standard samples;

(4) according to the spectrograms of the testing sample and the standard samples, the contents of chlorides and sulfides in the testing sample are calculated.

Said Eluent C is an aqueous solution of sodium nitrate, said developer $R_1$ is an aqueous solution of potassium bromate and said developer $R_2$ is an aqueous solution of indigo carmine-sulfuric acid.

In the above process, the condition for heating is 75-85° C., that is to say, the ambient temperature of 75-85° C. is a preferable condition for the continuous mixing of the mixture of developer $R_1$ and developer $R_2$, and Eluent C after mixing and entering into the reactor, and it is also a preferable condition for the continuous mixing and the reaction of the mixture of developer $R_1$ and developer $R_2$, and the eluent carrying a testing sample or a standard sample after mixing and entering into the reactor. Under the condition of 75-85° C., the reaction of developer $R_1$ and developer $R_2$ with the chloride ions and sulfide ions in the testing sample or the standard sample is more sufficient and is more favorable for improving the precision.

In the above process, the optimal formulations for the Eluent C, developer $R_1$ and developer $R_2$ are:

In Eluent C, the concentration of sodium nitrate is $1.0 \times 10^{-2}$ mmol/L-$1.2 \times 10^{-2}$ mmol/L; in developer $R_1$, the concentration of potassium bromate is 30.0 mmol/L-35.0 mmol/L; in developer $R_2$, the concentration of indigo carmine is 0.1 mmol/L-0.2 mmol/L and the concentration of sulfuric acid is 0.8 mol/L-1.0 mol/L.

In the above process, the optical path of the optical flow cell is 18 mm-25 mm, and the detection wavelength is at 605 nm-610 nm.

The invention offers the following advantageous effects:

1. A novel process for analyzing chlorides and sulfides in an aqueous sample is provided in the invention, and by adopting the process in the invention, the detection results for chlorides and sulfides can be obtained at the same time using a single apparatus, a single sample system and a single operation. Hence, time can be saved, the configuration of the analytic apparatus can be simplified and the analytic reagent can be reduced.

2. The requirements for both sensitivity and accuracy of the assay of chlorides and sulfides in environmental aqueous sample can be met by the process of the invention. The detection limit of chloride is 0.009 mg/L and the detection limit for sulfide is 0.002 mg/L.

3. The process of the invention is not only easy to operate, but also fast in analysis. Only 7-8 minutes are needed for a sample.

Figure 1:
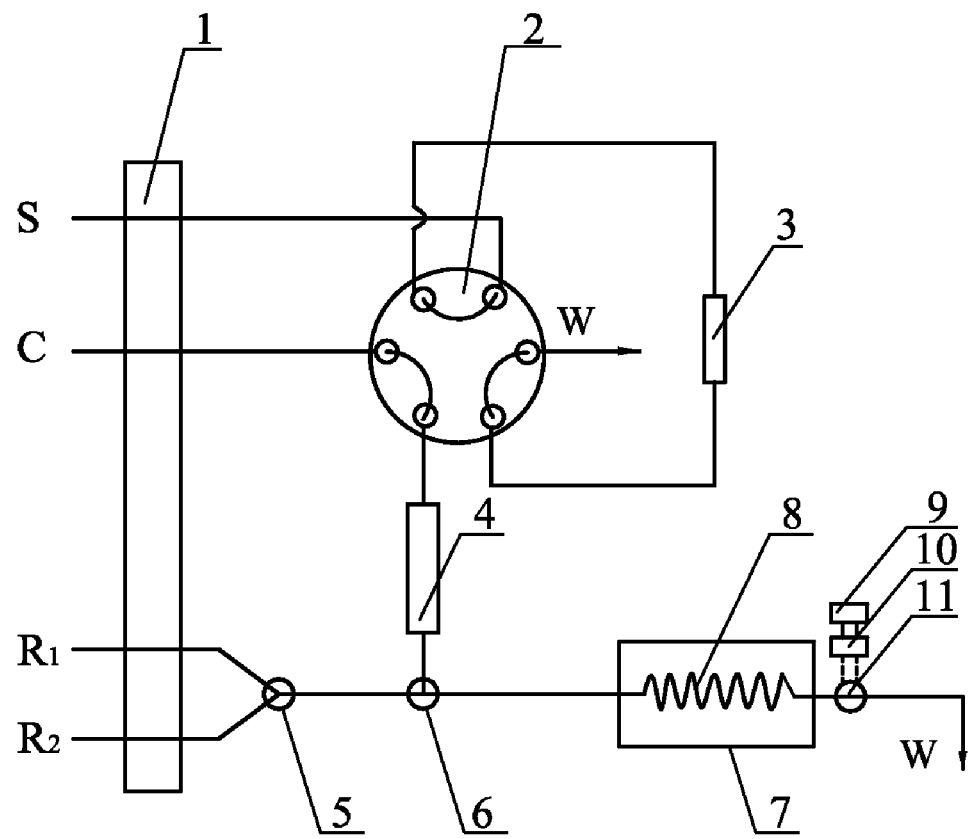
FIG. 1 is a schematic flow diagram of the low pressure ion exclusion charomatography for simultaneous analysis of chlorides and sulfides in the invention, and is also a schematic structural illustration of the analytic apparatus used therein, in which the apparatus is in its sampling status.

The symbols in FIG. 1-4 have the following meanings:

1—low pressure pump, 2—sampling valve, 3—sampling loop, 4—ion exclusion column, 5—a first mixer, 6—a second mixer, 7—heater, 8—reactor, 9—computer, 10—optical detector, 11—optical flow cell, S—standard sample or testing sample, C—Eluent, $R_1$—developer, $R_2$—developer and W—waster solution.

DETAILED DESCRIPTION OF THE INVENTION

The invention will be illustrated in more details by way of examples below.

Example 1

In this example, the testing sample was river water and the analysis was conducted as below.

1. Preparation of the Standard Samples (1) A primary reagent sodium chloride (NaCl) was placed into a crucible and after heated at 500-600° C. for 40-50 min and cooled, 0.1667 g sodium chloride was weighed and dissolved in small amount of de-ionized water and transferred into a 100 mL volumetric flask. After dilution to the reticle of the volumetric flask with de-ionized water, a mother liquid having a chloride ion concentration of 1000 mg/L was obtained.

(2) A certain amount of crystallized sodium sulfide ($Na_2S.9H_2O$) was placed into a Buchner filter or a small beaker, and the impurities on its surface was rinsed with water. After the moisture was absorbed by filter paper, 0.7506 g was weighed and dissolved in a small amount of de-ionized water and transferred into a 100 mL brown volumetric flask. After dilution to the reticle of the volumetric flask with de-ionized water, a mother liquid having a sulfide ion concentration of 1000 mg/L was obtained.

(3) 5 groups of standard samples were respectively prepared from the above mother liquids containing chloride ions and sulfide ions:

In the $1^{st}$ group: the concentration of chloride ion is 0.2 mg/L and the concentration of sulfide ion is 0.2 mg/L, In the $2^{nd}$ group: the concentration of chloride ion is 1.0 mg/L and the concentration of sulfide ion is 1.2 mg/L, In the $3^{rd}$ group: the concentration of chloride ion is 5.0 mg/L and the concentration of sulfide ion is 2.5 mg/L, In the $4^{th}$ group: the concentration of chloride ion is 10.0 mg/L and the concentration of sulfide ion is 4.5 mg/L, and In the $5^{th}$ group: the concentration of chloride ion is 20.0 mg/L and the concentration of sulfide ion is 7.0 mg/L.

2. Preparation of Eluent C 0.8500 g sodium nitrate was dissolved in 1000 mL de-ionized water so as to prepare a mother liquid of sodium nitrate with a concentration being 10.0 mmol/L. 1 mL of said mother liquid was drawn out and diluted to 1000 mL so as to formulate an eluent solution with a concentration of sodium nitrate being $1.0 \times 10^{-2}$ mmol/L.

3. Preparation of Developer $R_1$ 16.7000 g potassium bromate was dissolved in 1000 mL de-ionized water so as to prepare a solution of potassium bromate with a concentration being 0.1 mol/L. 30 mL of said 0.1 mol/L potassium bromate solution was drawn out and diluted to 100 mL so as to formulate a 30.0 mmol/L aqueous solution of potassium bromate as Developer $R_1$.

4. Preparation of Developer $R_2$ 0.4660 g indigo carmine was dissolved in 1000 mL de-ionized water so as to prepare a solution of indigo carmine with a concentration being 1.0 mmol/L. 15 mL of said 1.0 mmol/L indigo carmine solution and 20 mL sulfuric acid solution with a concentration being 4.0 mol/L were diluted into 100 mL by de-ionized water so as to formulate an aqueous solution of indigo carmine being 0.15 mmol/L and sulfuric acid being 0.8 mol/L as Developer $R_2$.

The chemicals used in the preparation of the standard samples, Eluent C and Developer $R_1$ and $R_2$ were all analytic pure.

5. Mapping of the Spectrogram of the Testing Sample

Figure 2:
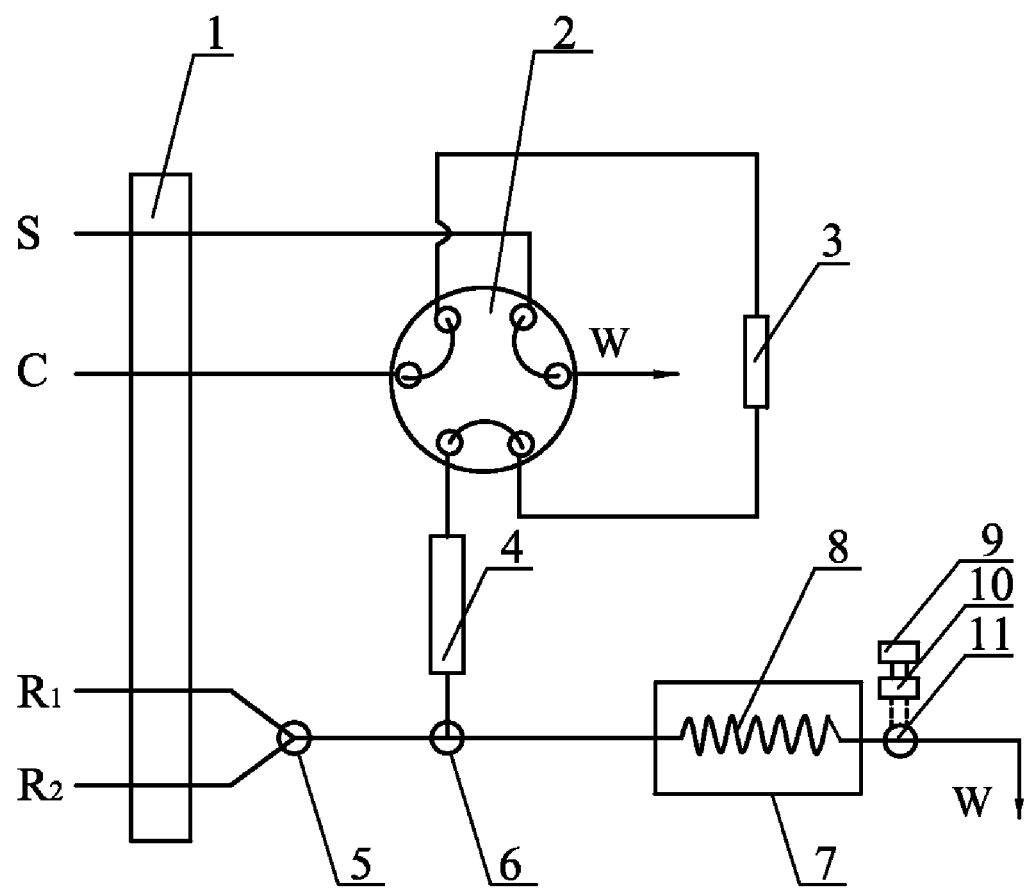
FIG. 2 is a schematic illustration of the apparatus in FIG. 1 in its analyzing status.

The assay was carried out using the automatic analytic apparatus as shown in FIG. 1 and FIG. 2. The low pressure pump 1 of the apparatus was a four-channel constant flow pump, whose capacity was 0.2-1.0 mL/min and working pressure was $2\times10^5$-$3\times10^5$ Pa. Sampling valve 2 was a six-channel automatic sampling valve. The section diameter of ion exclusion column 4 is φ6, the length was 110 mm and the filler in the column was anionic exchange resin having sulfonic acid group with a total exchange capacity, the particle diameter thereof was 30-35 μm, the exchange capacity is 3-4 mmol/g and said anionic exchange resin is market available product (Dowex 50, produced by Dow Chemicals) or it can be prepared by the user, the preparing method can be referred to ION EXCHANGE AND ADSORPTION RESIN (Binglin He, Wenqiang Huang, Shanghai Scientific and Technological Education Publishing House, February, 1995). A first mixer 5 and a second mixer 6 were three-channel structure. Heater 7 was an automatic constant temperature heater, with a digital display panel and an adjustable structure (manufactured by the laboratory of the present inventors, see ZL 20510020119.6). Reactor 8 was a reactor loop having a coil structure, and was coiled by polytetrafluoroethylene pipe with an inner diameter of 0.5 mm, a length of the reactor was 1.4 m. The optical path of optical flow cell 11 was 18 mm, the detection wavelength was 605 nm. The model of optical detector 10 was BSM202-31 (market available): the diameter of the optical aperture was 2.0 mm, the optical path was 1010 mm, the sampling volume was 3123 L. Computer 9 was ordinary PC machine.

Figure 3:
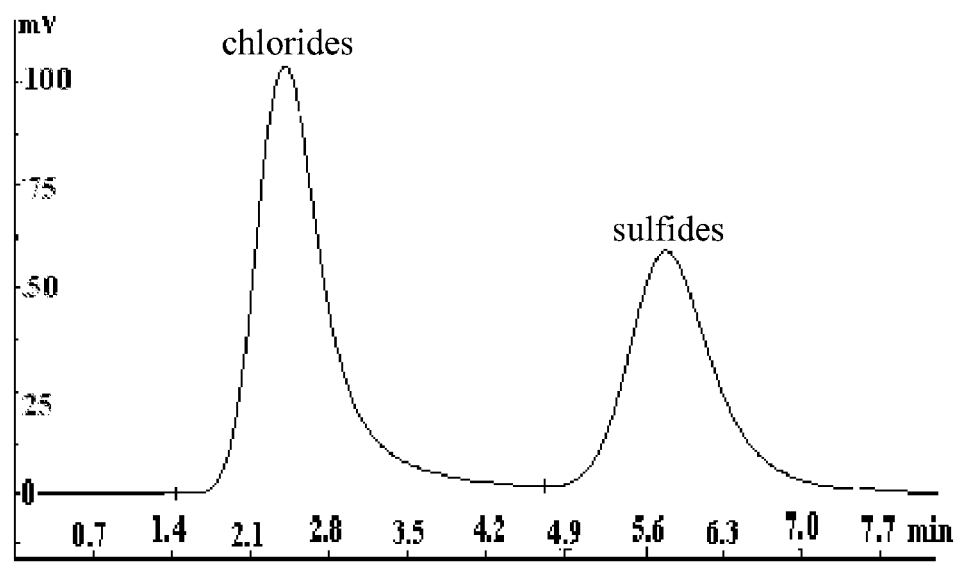
FIG. 3 is a spectrogram of a river water sample analyzed by the invention.

The base line was mapped firstly and the flow path of the apparatus was shown in FIG. 1: Driven by low pressure pump 1, the testing sample S entered into sampling valve 2 through the sample flow path and filled sampling loop 3 on the sampling valve; Eluent C flowed through the eluent flow path, sampling valve 2, ion exclusion column 4 and entered into the analytic detection flow path; developer $R_1$ and developer $R_2$ entered into the analytic detection flow path respectively through each developer flow path and mixed with each other in a first mixer 5 in the analytic detection flow path. In the analytic detection flow path, the mixture of developer $R_1$ and developer $R_2$ mixed with Eluent C in a second mixer 6 and then entered into reactor 8, and the mixing was continued at 75° C. (heater 7 being the heating resource). The resulting mixture flowed into optical flow cell 11. The absorbance of the mixture was collected by optical detector 10 and was converted into electric signals, which were shown on the screen of computer 9 as a stable baseline. After finishing the mapping of the baseline, the apparatus was automatically changed to "analyze" position under the control of a time relay. The flow path of the apparatus was shown in FIG. 2: Eluent C flowed through the eluent flow path, sampling valve 2, and entered into sampling valve 3; a testing sample S in sampling valve 3, under the drive of Eluent C, flowed into ion exclusion column 4 from the sampling loop, and entered into the analytic detection flow path through the ion exclusion column; developer $R_1$ and developer $R_2$ respectively entered into the analytic detection flow path through each developer flow path and mixed with each other in a first mixer 5 in the analytic detection flow path. In the analytic detection flow path, the mixture of developer $R_1$ and developer $R_2$ mixed with the Eluent C carrying the testing sample in a second mixer 6 and then entered into reactor 8 to continue the mixing at 75° C. (heater 7 being the heating resource). Reaction was occurred with color fading. The resulting mixture flowed into optical flow cell 11. The absorbance of the mixture was collected by optical detector 10 and was converted into electric signals, which were shown on the screen of the computer as a spectrogram of the testing sample, as shown in FIG. 3.

6. Mapping of the Spectrograms of the Standard Samples

The apparatus, Eluent C, Developer $R_1$ and Developer $R_2$ used for mapping the spectrograms of the standard samples were the same as those used for mapping the spectrogram of the testing sample, and the assay procedure was also the same. A series of spectrograms were obtained by testing each of the standard samples in the sequence of from the lowest concentration to the highest concentration.

7. Calculation of the Results of the Assay

The spectrogram of the testing sample was compared with those of the standard samples, and the content of the chlorides and sulfides in the test sample can be calculated accordingly.

The calculation was as follows:

TABLE 1

| | the concentrations of the standard samples and the corresponding peak heights in the spectrograms | | | | | |
|---|---|---|---|---|---|---|
| Chlorides | Concentrations of the standard samples (mg/L) $X_1$ | 0.2 | 1.0 | 5.0 | 10.0 | 20.0 |
| | Peak heights of the standard spectrogram (mV) $Y_1$ | 6.81 | 18.167 | 83.366 | 163.655 | 332.684 |
| Sulfides | Concentrations of the standard samples (mg/L) $X_2$ | 0.2 | 1.2 | 2.5 | 4.5 | 7.0 |
| | Peak heights of the standard spectrogram (mV) $Y_2$ | 1.269 | 37.993 | 102.508 | 209.794 | 339.413 |

Linear equations were derived from the data in Table 1:

$$Y_1 = 16.475 X_1 + 1.655, \text{ and}$$

$$Y_2 = 50.557 X_2 - 17.521$$

wherein "$Y_1$" is the peak height of the chlorides spectrogram (mV), "$X_1$" is the content of chlorides (mg/L), "$Y_2$" is the peak height of the sulfides spectrogram (mV), "$X_2$" is the content of sulfides (mg/L).

The peak heights of the chlorides and sulfides spectrogram for the river water testing sample were respectively 107.961 mV and 61.879 mV (see FIG. 3). According to the above equations, the contents of chlorides and sulfides were respectively calculated as 6.45 mg/L and 1.57 mg/L.

Example 2

In this example, the testing sample was lake water and the analysis was conducted as below.

1. Preparation of the Standard Samples (1) A primary reagent sodium chloride (NaCl) was placed into a crucible and after heated at 500-600° C. for 40-50 min and cooled, 0.1667 g sodium chloride was weighed and dissolved in small amount of de-ionized water and transferred into a 100 mL volumetric flask. After dilution to the reticle of the volumetric flask with de-ionized water, a mother liquid having a chloride ion concentration of 1000 mg/L was obtained.

(2) A certain amount of crystallized sodium sulfide ($Na_2S.9H_2O$) was placed into a Buchner filter or a small beaker, and the impurities on its surface was rinsed with water. After the moisture was absorbed by filter paper, 0.7506 g was weighed and dissolved in a small amount of de-ionized water and transferred into a 100 mL brown volumetric flask. After dilution to the reticle of the volumetric flask with de-ionized water, a mother liquid having a sulfide ion concentration of 1000 mg/L was obtained.

(3) 5 groups of standard samples were respectively prepared from the above mother liquids containing chloride ions and sulfide ions:

In the $1^{st}$ group: the concentration of chloride ion is 0.2 mg/L and the concentration of sulfide ion is 0.1 mg/L, In the $2^{nd}$ group: the concentration of chloride ion is 1.0 mg/L and the concentration of sulfide ion is 0.8 mg/L, In the $3^{rd}$ group: the concentration of chloride ion is 5.0 mg/L and the concentration of sulfide ion is 1.0 mg/L, In the $4^{th}$ group: the concentration of chloride ion is 10.0 mg/L and the concentration of sulfide ion is 2.5 mg/L, and In the $5^{th}$ group: the concentration of chloride ion is 16.0 mg/L and the concentration of sulfide ion is 3.5 mg/L.

2. Preparation of Eluent C 0.8500 g sodium nitrate was dissolved in 1000 mL de-ionized water so as to prepare a mother liquid of sodium nitrate with a concentration being 10.0 mmol/L. 1.2 mL of said mother liquid was drawn out and diluted to 1000 mL so as to formulate an eluent solution with a concentration of sodium nitrate being $1.2 \times 10^{-2}$ mmol/L.

3. Preparation of Developer $R_1$ 16.7000 g potassium bromate was dissolved in 1000 mL de-ionized water so as to prepare a solution of potassium bromate with a concentration being 0.1 mol/L. 35 mL of said 0.1 mol/L potassium bromate solution was drawn out and diluted to 100 mL so as to formulate a 35.0 mmol/L aqueous solution of potassium bromate as Developer $R_1$.

4. Preparation of Developer $R_2$ 0.4660 g indigo carmine was dissolved in 1000 mL de-ionized water so as to prepare a solution of indigo carmine with a concentration being 1.0 mmol/L. 20 mL of said 1.0 mmol/L indigo carmine solution and 25 mL sulfuric acid solution with a concentration being 4.0 mol/L were diluted into 100 mL by de-ionized water so as to formulate an aqueous solution of indigo carmine being 0.2 mmol/L and sulfuric acid being 1.0 mol/L as Developer $R_2$.

The chemicals used in the preparation of the standard samples, Eluent C and Developer $R_1$ and $R_2$ were all analytic pure.

5. Mapping of the Spectrogram of the Testing Sample

The assay was carried out using the automatic analytic apparatus as shown in FIG. 1 and FIG. 2. The optical path of optical flow cell 11 in the apparatus was 25 mm, the detection wavelength was 610 nm. Low pressure pump 1, sampling valve 2, ion exclusion column 4, a first mixer 5, a second mixer 6, heater 7, reactor 8, computer 9 and optical detector 10 were the same as those in Example 1.

Figure 4:
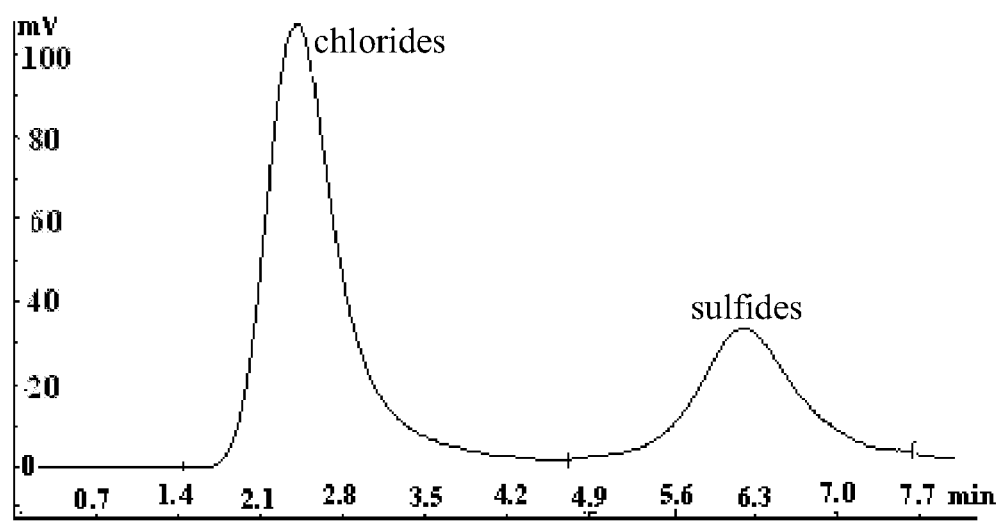
FIG. 4 is a spectrogram of a lake water sample analyzed by the invention.

The base line was mapped firstly and the flow path of the apparatus was shown in FIG. 1: Driven by low pressure pump 1, the testing sample S entered into sampling valve 2 through the sample flow path and filled sampling loop 3 on the sampling valve; Eluent C flowed through the eluent flow path, sampling valve 2, ion exclusion column 4 and entered into the analytic detection flow path; developer $R_1$ and developer $R_2$ entered into the analytic detection flow path respectively through each developer flow path and mixed with each other in a first mixer 5 in the analytic detection flow path. In the analytic detection flow path, the mixture of developer $R_1$ and developer $R_2$ mixed with Eluent C in a second mixer 6 and then entered into reactor 8, and the mixing was continued at 85° C. (heater 7 being the heating resource). The resulting mixture flowed into optical flow cell 11. The absorbance of the mixture was collected by optical detector 10 and was converted into electric signals, which were shown on the screen of computer 9 as a stable baseline. After finishing the mapping of the baseline, the apparatus was automatically changed to "analyze" position under the control of a time relay. The flow path of the apparatus was shown in FIG. 2: Eluent C flowed through the eluent flow path, sampling valve 2, and entered into sampling valve 3; a testing sample S in sampling valve 3, under the drive of Eluent C, flowed into ion exclusion column 4 from the sampling loop, and entered into the analytic detection flow path through the ion exclusion column; developer $R_1$ and developer $R_2$ respectively entered into the analytic detection flow path through each developer flow path and mixed with each other in a first mixer 5 in the analytic detection flow path. In the analytic detection flow path, the mixture of developer $R_1$ and developer $R_2$ mixed with the Eluent C carrying the testing sample in a second mixer 6 and then entered into reactor 8 to continue the mixing at 85° C. (heater 7 being the heating resource). Reaction was occurred with color fading. The resulting mixture flowed into optical flow cell 11. The absorbance of the mixture was collected by optical detector 10 and was converted into electric signals, which were shown on the screen of the computer as a spectrogram of the testing sample, as shown in FIG. 4.

6. Mapping of the Spectrograms of the Standard Samples

The apparatus, Eluent C, Developer $R_1$ and Developer $R_2$ used for mapping the spectrograms of the standard samples were the same as those used for mapping the spectrogram of the testing samples, and the assay procedure was also the same. A series of spectrograms were obtained by testing each of the standard samples in the sequence of from the lowest concentration to the highest concentration.

7. Calculation of the Results of the Assay

The spectrogram of the testing sample was compared with those of the standard samples, and the content of the chlorides and sulfides in the test sample can be calculated accordingly.

The calculation was as follows:

TABLE 2 the concentrations of the standard samples and the corresponding peak heights in the spectrograms

| Chlorides | Concentrations of the standard samples (mg/L) $X_1$ | 0.2 | 1.0 | 5.0 | 10.0 | 16.0 |
|---|---|---|---|---|---|---|
| | Peak heights of the standard spectrogram (mV) $Y_1$ | 9.081 | 23.507 | 111.951 | 222.778 | 366.277 |

TABLE 2-continued the concentrations of the standard samples and the
corresponding peak heights in the spectrograms

| Sulfides | Concentrations of the standard samples (mg/L) $X_2$ | 0.1 | 0.8 | 1.0 | 2.5 | 3.5 |
|---|---|---|---|---|---|---|
| | Peak heights of the standard spectrogram (mV) $Y_2$ | 10.37 | 81.919 | 110.84 | 283.497 | 398.004 |

Linear equations were derived from the data in Table 2:

$Y_1=22.608X_1+1.124$, and $Y_2=114.95X_2-4.698$ wherein "$Y_1$" is the peak height of the chlorides spectrogram (mV), "$X_1$" is the content of chlorides (mg/L), "$Y_2$" is the peak height of the sulfides spectrogram (mV), "$X_2$" is the content of sulfides (mg/L).

The peak heights of the chlorides and sulfides spectrogram for the lake water testing sample were respectively 108.692 mV and 33.946 mV (see FIG. 4). According to the above equations, the contents of chlorides and sulfides were respectively calculated as 4.76 mg/L and 0.35 mg/L.

The invention claimed is:

1. A process for simultaneous assay of chlorides and sulfides by low pressure ion exclusion chromatography, wherein an analytic apparatus comprising a sample flow path, an eluent flow path, a developer flow path, a sampling valve, a sampling loop, an ion exclusion column and an analytic detection flow path is used, and the working pressure of said analytic apparatus is $2 \times 10^5$-$3 \times 10^5$ Pa, said analytic detection flow path includes a mixer, a reactor and an optical flow cell, said process comprises the following steps:
   (1) Eluent C flows through the eluent flow path, the sampling valve, the ion exclusion column and enters into the analytic detection flow path; developer $R_1$ and developer $R_2$ respectively enter into the analytic detection flow path through each developer flow path and mix with each other in the analytic detection flow path; in the analytic detection flow path, the mixture of developer $R_1$ and developer $R_2$ mixes with Eluent C and then enters into the reactor, and the mixing is continued under heating, the resulting mixture flows into the optical flow cell and a baseline is mapped accordingly;
   (2) a testing sample S flows into the sampling loop through the sample flow path and the sampling valve, and under the drive of Eluent C, flows into the ion exclusion column from the sampling loop, and enters into the analytic detection flow path through the ion exclusion column; developer $R_1$ and developer $R_2$ each enter into the analytic detection flow path through respective developer flow path and mix with each other in the analytic detection flow path; in the analytic detection flow path, the mixture of developer $R_1$ and developer $R_2$ mixes with the Eluent C carrying the testing sample and then enters into the reactor, and the mixing is continued under heating and a reaction takes place, the reacted mixture flows into the optical flow cell and a spectrogram of the testing sample is mapped accordingly;
   (3) a series of standard samples with known concentrations of chlorides and sulfides are used to replace the testing sample, and steps (1) and (2) are repeated so as to obtain a series of spectrograms of standard samples;
   (4) according to the spectrograms of the testing sample and the standard samples, the contents of chlorides and sulfides in the testing sample are calculated;
   wherein said Eluent C is an aqueous solution of sodium nitrate, said developer $R_1$ is an aqueous solution of potassium bromate and said developer $R_2$ is an aqueous solution of indigo carmine-sulfuric acid.

2. The process for simultaneous assay of chlorides and sulfides by low pressure ion exclusion chromatography according to claim 1, wherein the heating in each of step (1) and step (2) is at 75-85° C.

3. The process for simultaneous assay of chlorides and sulfides by low pressure ion exclusion chromatography according to claim 1, wherein in Eluent C, the concentration of sodium nitrate is $1.0 \times 10^{-2}$ mmol/L-$1.2 \times 10^{-2}$ mmol/L; in developer $R_1$, the concentration of potassium bromate is 30.0 mmol/L-35.0 mmol/L; in developer $R_2$, the concentration of indigo carmine is 0.1 mmol/L-0.2 mmol/L and the concentration of sulfuric acid is 0.8 mol/L-1.0 mol/L.

4. The process for simultaneous assay of chlorides and sulfides by low pressure ion exclusion chromatography according to claim 3, wherein the optical path of the optical flow cell is 18 mm-25 mm, and the detection wavelength is at 605 nm-610 nm.

5. The process for simultaneous assay of chlorides and sulfides by low pressure ion exclusion chromatography according to claim 2, wherein the optical path of the optical flow cell is 18 mm-25 mm, and the detection wavelength is at 605 nm-610 nm.

6. The process for simultaneous assay of chlorides and sulfides by low pressure ion exclusion chromatography according to claim 1, wherein in Eluent C, the concentration of sodium nitrate is $1.0 \times 10^{-2}$ mmol/L-$1.2 \times 10^{-2}$ mmol/L; in developer $R_1$, the concentration of potassium bromate is 30.0 mmol/L-35.0 mmol/L; in developer $R_2$, the concentration of indigo carmine is 0.1 mmol/L-0.2 mmol/L and the concentration of sulfuric acid is 0.8 mol/L-1.0 mol/L.

7. The process for simultaneous assay of chlorides and sulfides by low pressure ion exclusion chromatography according to claim 6, wherein the optical path of the optical flow cell is 18 mm-25 mm, and the detection wavelength is at 605 nm-610 nm.

8. The process for simultaneous assay of chlorides and sulfides by low pressure ion exclusion chromatography according to claim 1, wherein the optical path of the optical flow cell is 18 mm-25 mm, and the detection wavelength is at 605 nm-610 nm.

* * * * *